(12) United States Patent
Wittenberger

(10) Patent No.: US 9,089,314 B2
(45) Date of Patent: Jul. 28, 2015

(54) PARTIALLY COMPLIANT BALLOON DEVICE

(75) Inventor: Dan Wittenberger, L'ile Bizard (CA)

(73) Assignee: Medtronic CryoCath LP, Toronto, Ontario (CA)

(*) Notice: Subject to any disclaimer, the term of this patent is extended or adjusted under 35 U.S.C. 154(b) by 1023 days.

(21) Appl. No.: 12/694,938

(22) Filed: Jan. 27, 2010

(65) Prior Publication Data

US 2011/0184399 A1   Jul. 28, 2011

(51) Int. Cl.
*A61B 18/02* (2006.01)
*A61B 18/00* (2006.01)

(52) U.S. Cl.
CPC ......... *A61B 18/02* (2013.01); *A61B 2018/0022* (2013.01); *A61B 2018/00255* (2013.01); *A61B 2018/00375* (2013.01); *A61B 2018/0212* (2013.01)

(58) Field of Classification Search
CPC ........... A61B 2018/00023; A61B 2018/00011; A61B 2018/00005; A61B 2018/00255; A61B 2018/0212; A61B 2018/0262; A61B 2018/0022; A61B 18/02
USPC .................................. 606/21, 22; 604/101.02
See application file for complete search history.

(56) References Cited

U.S. PATENT DOCUMENTS

| | | | | |
|---|---|---|---|---|
| 4,417,576 A | * | 11/1983 | Baran | 128/207.15 |
| 5,308,325 A | | 5/1994 | Quinn et al. | |
| 5,536,252 A | * | 7/1996 | Imran et al. | 604/101.02 |
| 5,971,979 A | * | 10/1999 | Joye et al. | 606/21 |
| 6,132,397 A | * | 10/2000 | Davis et al. | 604/101.02 |
| 6,283,959 B1 | * | 9/2001 | Lalonde et al. | 606/21 |
| 6,514,245 B1 | * | 2/2003 | Williams et al. | 606/21 |
| 6,575,966 B2 | | 6/2003 | Lane et al. | |
| 6,595,988 B2 | | 7/2003 | Wittenberger et al. | |
| 7,300,433 B2 | | 11/2007 | Lane et al. | |
| 7,524,274 B2 | | 4/2009 | Patrick et al. | |
| 2002/0007180 A1 | * | 1/2002 | Wittenberger et al. | 606/21 |
| 2002/0045892 A1 | * | 4/2002 | Kramer | 606/21 |
| 2002/0045894 A1 | * | 4/2002 | Joye et al. | 606/21 |
| 2002/0156469 A1 | * | 10/2002 | Yon et al. | 606/21 |
| 2002/0169489 A1 | * | 11/2002 | Dobak III et al. | 607/105 |
| 2003/0187428 A1 | * | 10/2003 | Lane et al. | 606/21 |

(Continued)

FOREIGN PATENT DOCUMENTS

CA   2666334 A1   8/2002
WO   2009037710 A2   3/2009

OTHER PUBLICATIONS

Dow Chemical, A Guide to Glycols, pp. 1-58, http://www.dow.com/PublishedLiterature/dh_0047/0901b803800479d9.pdf, accessed Dec. 8, 2012.*

*Primary Examiner* — Joseph Stoklosa
*Assistant Examiner* — Jocelyn D Ram
(74) *Attorney, Agent, or Firm* — Christopher & Weisberg, P.A.

(57) ABSTRACT

A medical device is provided, having an elongate body defining a distal portion and a proximal portion; a first expandable member disposed on the distal portion of the elongate body and defining a cooling chamber therein, the first expandable member having a first rigidity; a second expandable member disposed around the first expandable member to define an interstitial region therebetween, where the second expandable member has a second rigidity less than the first rigidity; a gel disposed within the interstitial region; a coolant flow path in fluid communication with the cooling chamber; and a cryogenic coolant source in fluid communication with the coolant flow path.

9 Claims, 3 Drawing Sheets

(56) References Cited

U.S. PATENT DOCUMENTS

| | | | |
|---|---|---|---|
| 2003/0199861 A1* | 10/2003 | Lafontaine | 606/21 |
| 2006/0178663 A1* | 8/2006 | LaFontaine | 606/21 |
| 2006/0270982 A1* | 11/2006 | Mihalik et al. | 604/113 |
| 2007/0255394 A1 | 11/2007 | Ryan | |
| 2008/0078403 A1* | 4/2008 | Clayton | 128/207.15 |
| 2008/0200829 A1 | 8/2008 | Abboud et al. | |
| 2008/0300571 A1 | 12/2008 | LePivert | |
| 2009/0234345 A1* | 9/2009 | Hon | 606/21 |
| 2009/0281533 A1* | 11/2009 | Ingle et al. | 606/21 |
| 2010/0069900 A1* | 3/2010 | Shirley et al. | 606/21 |
| 2010/0286678 A1* | 11/2010 | Weber et al. | 606/21 |
| 2011/0190751 A1* | 8/2011 | Ingle et al. | 606/21 |

* cited by examiner

PARTIALLY COMPLIANT BALLOON DEVICE

CROSS-REFERENCE TO RELATED APPLICATION

N/A

STATEMENT REGARDING FEDERALLY SPONSORED RESEARCH OR DEVELOPMENT

N/A

FIELD OF THE INVENTION

The present invention relates to medical methods and systems for tissue treatment, and in particular, to catheters for thermal tissue treatment.

BACKGROUND OF THE INVENTION

Minimally invasive surgical techniques are known for performing medical procedures within all parts of the cardiovascular system. Exemplary known procedures include the steps of passing a small diameter, highly-flexible catheter through one or more blood vessels and into the heart. When positioned as desired, additional features of the catheter are used, in conjunction with associated equipment, to perform all or a portion of a medical treatment, such as vessel occlusion, tissue biopsy, or tissue ablation, among others. Almost always, these procedures are performed while the heart is beating and blood is flowing. Not surprisingly, even though visualization and positioning aids are adequate for general placement of the device, maintaining the device in a selected position and orientation can be difficult as the tissue moves and blood flows, especially during a procedure that must be done quickly. As diagnostic and visualization equipment and techniques have continued to evolve, it has become possible to identify tissue areas to be treated with greater precision than the ability to quickly situate the device and effectuate treatment.

In addition to the challenges presented by moving tissue and flowing blood, the actual topography of the tissue being treated presents challenges. For example, unlike stylized drawings that depict the interior of the chambers of the heart as having smooth, evenly curved walls leading neatly to tubular blood vessels, the interior surfaces of the heart's chambers are irregular, uneven, and fibrous, as are the openings to blood vessels. Thus, for procedures that call for uniform tissue contact or tissue contact along an extended line, the structure and techniques for use of known devices can be deficient in some regards. For example, difficulties may arise in properly placing and holding a device in position at the desired orientation due to the uneven topography of the targeted tissue. Further, even if the device is suitable for the tissue topography at the treatment site, variations in physiological anatomy may occur from one patient to the next, further complicating the use of a particularly-dimensioned device. Additional difficulty may stem from applying excessive force to the device to maintain contact between the device and the tissue, instead resulting in tissue damage or the inadvertent displacement of the device downstream in a particular vessel or organ.

By way of example, catheter-based devices are known for placement in the left atrium for ablating tissue within the atrium for the purpose of electrically isolating one or more pulmonary veins from the atrium in an attempt to increase the success rate of atrial fibrillation ablation. Given the uneven topography of the tissue, anatomical differences between patients, and the tortuous environment of the blood flowing through the vasculature mentioned above, secure placement of a device against a pulmonary vein can be challenging. Moreover, if too much force is applied to the device and thus the tissue, risk of damaging the pulmonary vein increases— e.g., the vein could be deformed, ruptured, stenosed, or otherwise injured. In view of the above, it would be desirable to provide a medical device and treatment methods of use thereof that allow for secure placement against uneven, topographical surfaces such as those found in the left atrium of the heart while reducing or otherwise minimizing the risk of unwanted injury to the tissue region being treated.

SUMMARY OF THE INVENTION

The present invention advantageously provides a medical device and treatment methods of use thereof that allow for secure placement against uneven, topographical surfaces such as those found in the left atrium of the heart while reducing or otherwise minimizing the risk of unwanted injury to the tissue region being treated. In particular, an intravascular catheter is provided, including a first expandable member disposed on a distal portion of the catheter; a second expandable member disposed within the first expandable member to define an interstitial region therebetween; a interstitial agent disposed within the interstitial region, the interstitial agent comprising a liquid—e.g. saline, contrast solution or a mixture thereof, or gel; a coolant flow path in fluid communication with the cooling chamber; and a cryogenic coolant source in fluid communication with the coolant flow path. The intravascular catheter may also include a second flow path in fluid communication with the interstitial region, and the interstitial agent may be a liquid or a gel having a viscosity between approximately 0.6 cP and approximately 2000 cP and a thermal conductivity between approximately 0.1 W/(mK) and approximately 1.0 W/(mK). The intravascular catheter may also include a fluid ingress detection element in communication with the cooling chamber, the ingress detection element sensing an ingress of fluid into the cooling chamber from the interstitial region.

A medical device is also provided, including an elongate body defining a distal portion and a proximal portion; a first expandable member disposed on the distal portion of the elongate body and defining a cooling chamber therein, the first expandable member having a first rigidity; a second expandable member disposed around the first expandable member to define an interstitial region therebetween, and where the second expandable member has a second rigidity less than the first rigidity; a liquid or a gel disposed within the interstitial region; a coolant flow path in fluid communication with the cooling chamber; and a cryogenic coolant source in fluid communication with the coolant flow path. The second expandable member may be attached to at least one of the elongate body and the first expandable member, thereby sealing the interstitial region. Also, a second flow path may be provided in fluid communication with the interstitial region.

A method for operating a medical device is also disclosed, including positioning the medical device proximate a cardiac tissue region, the medical device including a gel interposed between a first expandable element and a second expandable element disposed within the first expandable element; applying a vacuum to the second expandable element; detecting whether gel ingresses into the second expandable element; and generating an alert based at least in part on the detection. The method may also include delivering coolant into the second expandable element through an injection lumen;

introducing the gel between the first and second expandable elements through an interstitial lumen; terminating coolant delivery; controllably evacuating coolant from the second expandable element; and controllably evacuating the gel. In addition, positioning the medical device proximate target tissue can include routing at least a portion of the medical device through a blood vessel and positioning the first expandable element proximate a pulmonary vein.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
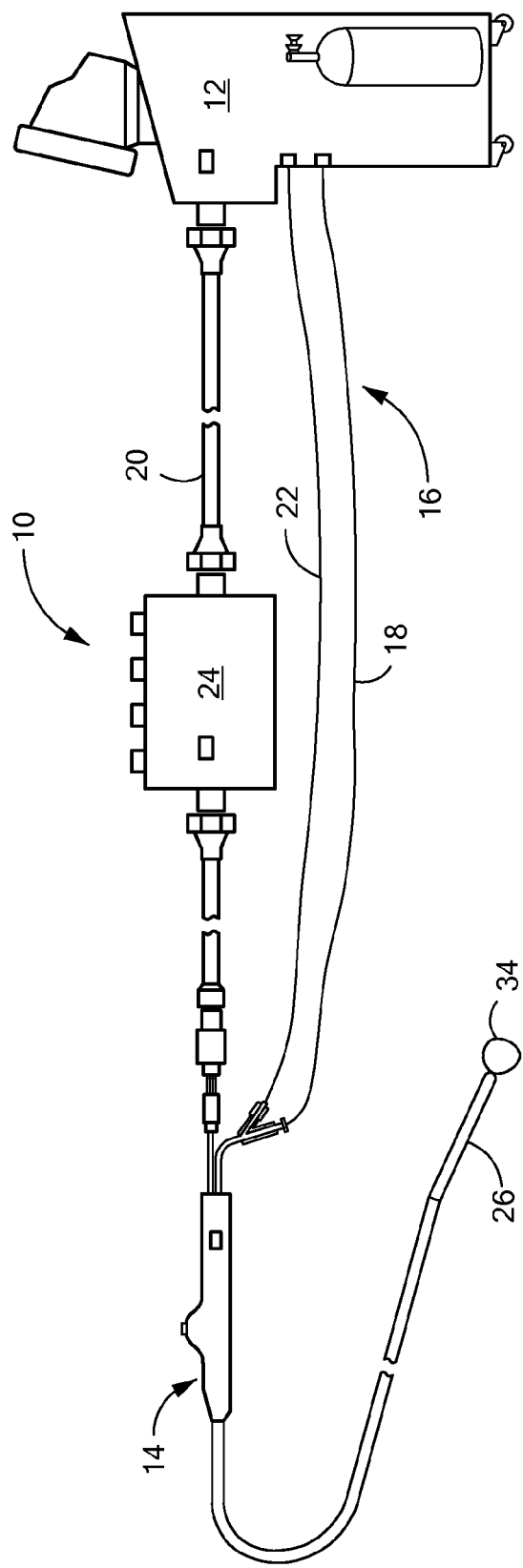
FIG. 1 is an illustration of an embodiment of a medical system constructed in accordance with the principles of the present invention.

A medical device and methods of use thereof are provided herein that allow for secure placement and positioning of a medical device against uneven, topographical surfaces such as those found in the left atrium of the heart while reducing or otherwise minimizing the risk of unwanted injury to the tissue region being treated. Referring now to the drawing figures in which like reference designations refer to like elements, an embodiment of a medical system constructed in accordance with principles of the present invention is shown in FIG. 1 and generally designated as "10." The system generally includes a cooling unit or console 12 coupled to a medical device 14 through an umbilical system 16. The medical device 14 may be a medical probe, a catheter, a balloon-catheter, as well as other devices deliverable or otherwise positionable through the vasculature and/or proximate to a tissue region for treatment. In particular, the medical device 14 may include a device operable to thermally treat a selected tissue site, including cardiac tissue. The medical system 10 may also include one or more sensors to monitor the operating parameters throughout the system, including for example, pressure, temperature, flow rates, volume, or the like in the console 12, the umbilical system 16, and/or the medical device 14.

Umbilical system 16 may include three separate umbilicals: a coaxial cable umbilical 18, an electrical umbilical 20 and a vacuum umbilical 22. An outer vacuum umbilical may be suitable for a medical device having multiple layers or balloons. If the user wishes to perform a radiofrequency ("RF") ablation procedure, radiofrequency energy can be provided to electrodes on the medical device 14 via electrical umbilical 20 to perform an RF ablation technique. Electrical umbilical 20 can include an electrocardiograph ("ECG") box 24 to facilitate a connection from one or more electrodes on the medical device 14 to an ECG monitor (not shown). Coaxial umbilical 18 may include both a cooling injection umbilical and a vacuum umbilical that provide respective inlet and return paths for a refrigerant or coolant used to cool a tissue-treating section of the device 14. The vacuum umbilical 22 may provide a safety conduit allowing excess coolant or gas to escape from the device 14 if the pressure within the medical device 14 exceeds a predefined limit. The vacuum umbilical 22 can also be used to capture air through a leak of the outer vacuum system where it is outside the patient and as a lumen to ingress blood when inside the patient.

Figure 2:
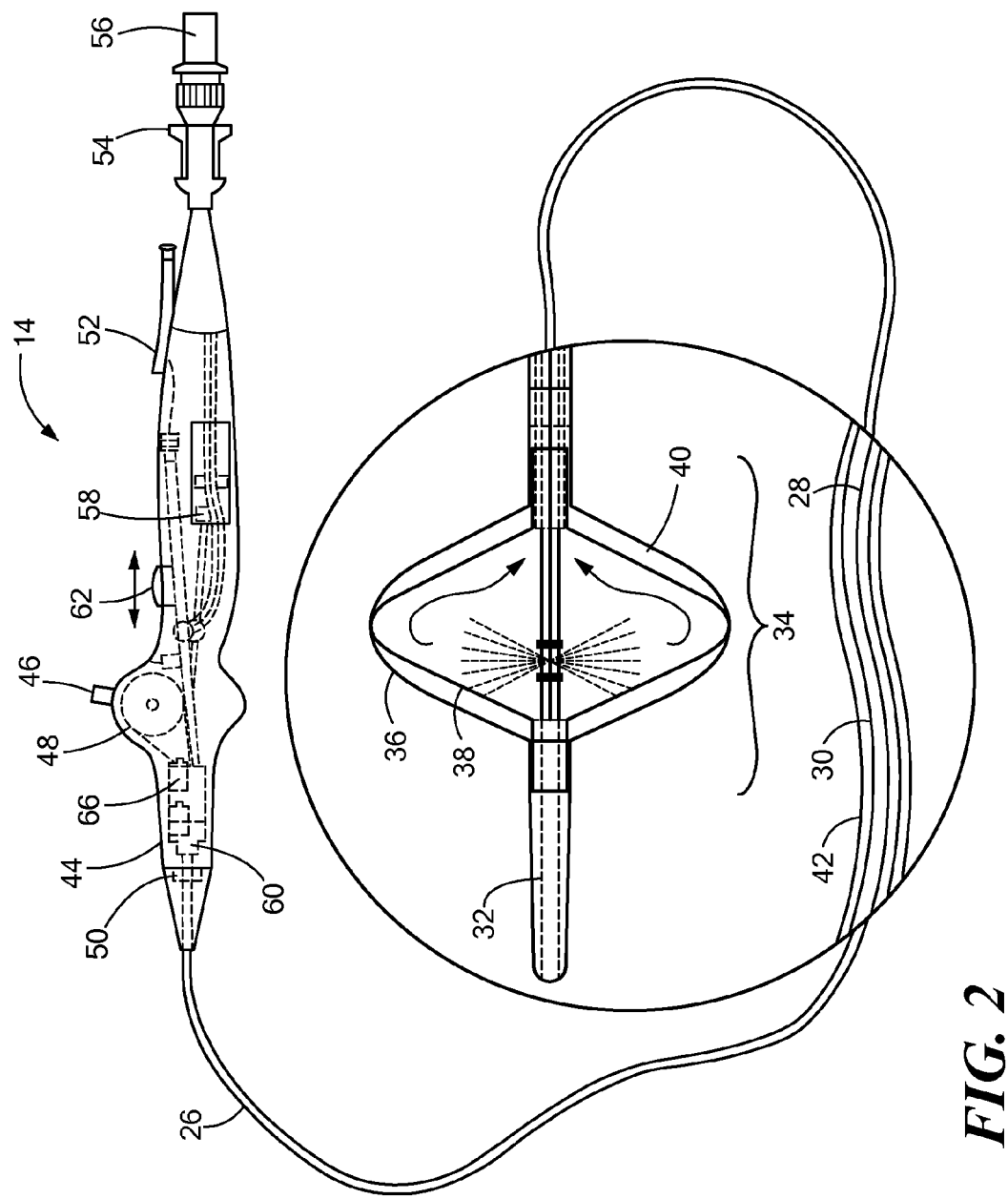
FIG. 2 is an illustration of an embodiment of a medical device constructed in accordance with the principles of the present invention.

Now referring to FIG. 2, the medical device 14 is shown in more detail. The medical device 10 may include an elongate body 26 passable through a patient's vasculature. The elongate body 26 may define a proximal portion and a distal portion, and may further include one or more lumens disposed within the elongate body 26 thereby providing mechanical, electrical, and/or fluid communication between the proximal portion of the elongate body 26 and the distal portion of the elongate body 26. For example, the elongate body 26 may include an injection lumen 28 and an exhaust lumen 30 defining a fluid flow path therethrough. In addition, the elongate body 26 may include a guidewire lumen 32 movably disposed within and/or extending along at least a portion of the length of the elongate body 26 for over-the-wire applications. The guidewire lumen 32 may define a proximal end and a distal end, and the guidewire lumen 32 may be movably disposed within the elongate body 26 such that the distal end of the guidewire lumen 32 extends beyond and out of the distal portion of the elongate body 26.

The medical device may include a treatment region 34 for energetic or other therapeutic interaction between the medical device 14 and a treatment site. The treatment region 34 may include a thermal treatment element, such as an expandable membrane or balloon and/or one or more electrodes or other thermally-transmissive components, at least partially disposed on the elongate catheter body. In a particular example, the treatment region may include a first expandable/inflatable element or balloon 36 defining a proximal end coupled to the distal portion of the elongate body 26 of the medical device 14, while further defining a distal end coupled to the distal end of the guidewire lumen 32. As such, due to the movable nature of the guidewire lumen 32 about the elongate body 26, any axial and/or longitudinal movement of the guidewire lumen 32 may act to tension or loosen the first expandable element 36, i.e., extend or retract the expandable element 36 from a lengthened state to a shortened state during an inflation or deflation thereof. In addition, the first expandable element 36 may have any of a myriad of shapes, and may further include one or more material layers providing for puncture resistance, radiopacity, or the like. The first expandable element 36 may be in communication with the fluid injection and exhaust lumens of the medical device 14 as described above.

The medical device 14 may further include a second expandable/inflatable element or balloon 38 contained within or otherwise encompassed by the first expandable element 36 such that an interstitial region, envelope or space 40 is defined therebetween. The second expandable element 38 may be in communication with the fluid injection and exhaust lumens of the medical device 14 as described above, i.e., a fluid flow path may provide an inflation fluid or coolant, such as a cryogenic fluid or the like, to the interior of the second expandable element 38. Further, the interstitial region 40 may be in fluid communication with an interstitial lumen 42 providing a fluid flow path or avenue separate and independent from a fluid flow path delivering fluid or otherwise in communication with an interior of the second expandable element 38. The second pathway provides an alternate exhaust route for fluid that may leak from the interior of the second expandable element 38 into the interstitial region 40 or fluid entering the medical device 14 from the exterior. In particular, the isolation of the interstitial lumen 42 from the interior of the second expandable element 38 provides an alternate route for fluid to circulate in the case of a rupture or leak of either the first or second expandable elements, as well as allowing for the injection or circulation of fluids within the interstitial region 40 independently of fluids directed towards the second expandable element 38. Towards that end, the interstitial region may be in fluid communication with a fluid source, a vacuum source, or the like separate from a fluid source, vacuum source or otherwise in fluid communication with the interior of the second expandable element 38. Alternatively, the interstitial lumen 42 may be joined to or otherwise in fluid communication with the injection lumen 28 and the interior of the second expandable element 38 to provide a single exhaust or vacuum source for the medical device 14.

While the first and second expandable elements 36,38 may have any of a myriad of shapes, and may include one or more material layers or components providing for puncture resistance, radiopacity, or the like, they may further include rigidity and/or expansion characteristics different from one another to facilitate the passage of the medical device 14 through the vasculature and/or placement or positioning of the treatment region 34 proximate a targeted tissue area. For example, the first expandable element 36 may have a rigidity less than a rigidity of the second expandable element 38. The decreased rigidity and increased pliability of the first, "outer" expandable element 36 may provide for increased deformation or pliability when in contact with a targeted tissue area, while the increased rigidity and decreased pliability of the second, "inner" expandable element 38 provides a stronger, reinforcing structure that aids in ensuring the treatment region 34 does not reduce or collapse beyond a predetermined or selected dimension. As discussed above, such unwanted collapsing, forceful decrease in diameter or excessive application of force between the treatment region 34 and a targeted tissue, such as a pulmonary vein, could result in the unwanted downstream passage of the medical device and resulting injury to the vein. In a particular example, the first, "outer" expandable element 36 may be constructed from highly compliant polyurethane, while the second, "inner" expandable element 38 may be constructed from non-compliant polyester. The second expandable element 38 may further be constructed to have a maximum expanded diameter of approximately 20 mm to approximately 32 mm for applications involving one or more pulmonary veins.

The interstitial region 40 may include or otherwise contain an interstitial cushioning and/or insulating agent 43 to facilitate the positioning, contact and thermal exchange between the treatment region 34 and targeted tissue area. For example, the interstitial agent 43 may include a gel or a liquid including saline, contrast solution or a mixture thereof. The liquid or the gel may provide thermal insulative properties enabling certain portions of the treatment region 34 to more readily conduct thermal energy between the medical device 14 and a targeted tissue area, while shielding or reducing the thermal exchange and conductivity of other portions of the treatment region 34. In particular, the gel may provide a thermal conductivity ranging between approximately 0.1 W/(mK) and approximately 1.0 W/(mK).

The interstitial agent 43 may further act as a deformational, cushioning intermediary between the deformational or rigidity characteristics of the first expandable element 36 and the deformational or rigidity characteristics of the second expandable element 38. For example, when positioned against a targeted tissue area with an applied force, the first expandable element 36 may deform or otherwise pliably conform to the contacted tissue area. The pliable conformation of the first expandable element 36 may result in the compression or movement of the interstitial agent 43 within the interstitial region 40, while still providing for a degree of pliability and deformational ability exceeding that of the more-rigid second expandable element 38. The compression, deformation, and/or movement of the interstitial agent 43 may be limited by the composition and viscosity of the interstitial agent, where the viscosity may range between approximately 0.6 cP and approximately 2000 cP, for example.

The interstitial agent 43 may be introduced into the treatment region 34 of the medical device (through the interstitial lumen 42 for example) prior to insertion of the medical device 14 into a patient, or afterwards upon locating the device in the approximate position for treatment. Alternatively, the interstitial agent 43 may be provided and sealed within the interstitial region 40 prior to insertion or use within a patient.

The medical device 14 may further include one or more temperature and/or pressure sensors (not shown) proximate the treatment region for monitoring, recording or otherwise conveying measurements of conditions within the medical device 14 or the ambient environment at the distal portion of the medical device 14. The sensor(s) may be in communication with the console 12 for initiating or triggering one or more alerts or therapeutic delivery modifications during operation of the medical device 14.

The medical device 14 may include a handle 44 coupled to the proximal portion of the elongate body 26, where the handle may include an element such as a lever or knob 46 for manipulating the catheter body and/or additional components of the medical device 14. For example, a pull wire 48 with a proximal end and a distal end may have its distal end anchored to the elongate body 26 at or near the distal end. The proximal end of the pull wire 48 may be anchored to an element such as a cam in communication with and responsive to the lever 46.

The handle 44 can further include circuitry for identification and/or use in controlling of the medical device 14 or another component of the system. For example, the handle may include one or more pressure sensors 50 to monitor the fluid pressure within the medical device 14. Additionally, the handle may be provided with a fitting 52 for receiving a guidewire that may be passed into the guidewire lumen 32.

The handle 44 may also include connectors that are matable directly to a fluid supply/exhaust and control unit or indirectly by way of one or more umbilicals. For example, the handle may be provided with a first connector 54 that is matable with the co-axial fluid umbilical 18 and a second connector 56 that is matable with the electrical umbilical 20. The handle 44 may further include blood detection circuitry 58 in fluid and/or optical communication with the injection, exhaust and/or interstitial lumens. The handle 44 may also include a pressure relief valve 60 in fluid communication with the injection, exhaust and/or interstitial lumens to automatically open under a predetermined threshold value in the event that value is exceeded.

Continuing to refer to FIG. 2, in addition, the medical device 14 may include an actuator element 62 that is movably coupled to the proximal portion of the elongate body 26 and/or the handle 44. The actuator element 62 may further be coupled to the proximal portion of the guidewire lumen 32 such that manipulating the actuator element 62 in a longitudinal direction causes the guidewire lumen 32 to slide towards either of the proximal or distal portions of the elongate body 26. As a portion of either and/or both the first and second expandable elements 36, 38 may be coupled to the guidewire lumen 32, manipulation of the actuator element 62 may further cause the expandable element(s) to be tensioned or loosened, depending on the direction of movement of the actuator element 62, and thus, the guidewire lumen 32. Accordingly, the actuator element 62 may be used to provide tension on the expandable element(s) 36,38 during a particular duration of use of the medical device 14, such as during a deflation sequence, for example. The actuator element 62 may include a thumb-slide, a push-button, a rotating lever, or other mechanical structure for providing a movable coupling to the elongate body 26, the handle 44, and/or the guidewire lumen 32. Moreover, the actuator element 62 may be movably coupled to the handle 44 such that the actuator element 62 is movable into individual, distinct positions, and is able to be releasably secured in any one of the distinct positions.

The medical device 14 may include a leak detection system that monitors or measures one or more operating parameters of the system as an indication that the integrity of the medical device has been compromised. For example, one or more sensors 66 may be disposed on or about the first and second expandable elements 36, 38, the injection lumen 28, the exhaust lumen 30, and/or the interstitial lumen 42 to detect pressure, temperature, impedance, optical properties or the like of a medium flowing therethrough. The measured or monitored value may be compared to a predetermined threshold for the subsequent generation of an alert or termination of one or more functions of the system 10 should the threshold be exceeded. The sensors may be coupled to the console 12 for controlling or triggering an automated shut-down sequence or termination of system operation. When a leak develops in either the first expandable element 36 or second expandable element 38, the sensor(s) may detect such a leak and/or the flow of fluid and send a signal to the console 12 to interrupt or shut down coolant flow to the medical device 14, or to otherwise alter the operation of the overall system 10.

In an exemplary system, a fluid supply 64 including a coolant, cryogenic refrigerant, or the like, an exhaust or scavenging system (not shown) for recovering or venting expended fluid for re-use or disposal, as well as various control mechanisms for the medical system may be housed in the console 12. In addition to providing an exhaust function for the catheter fluid supply, the console 12 may also include pumps, valves, controllers or the like to recover and/or re-circulate fluid delivered to the handle 44, the elongate body 26, and treatment region 34 of the medical device 14. A vacuum pump in the console 12 may create a low-pressure environment in one or more conduits within the medical device 14 so that fluid is drawn into the conduit(s) of the elongate body 26, away from the treatment region 34, and towards the proximal end of the elongate body 26. The console 12 may include one or more controllers, processors, and/or software modules containing instructions or algorithms to provide for the automated operation and performance of the features, sequences, or procedures described herein.

Figure 3:
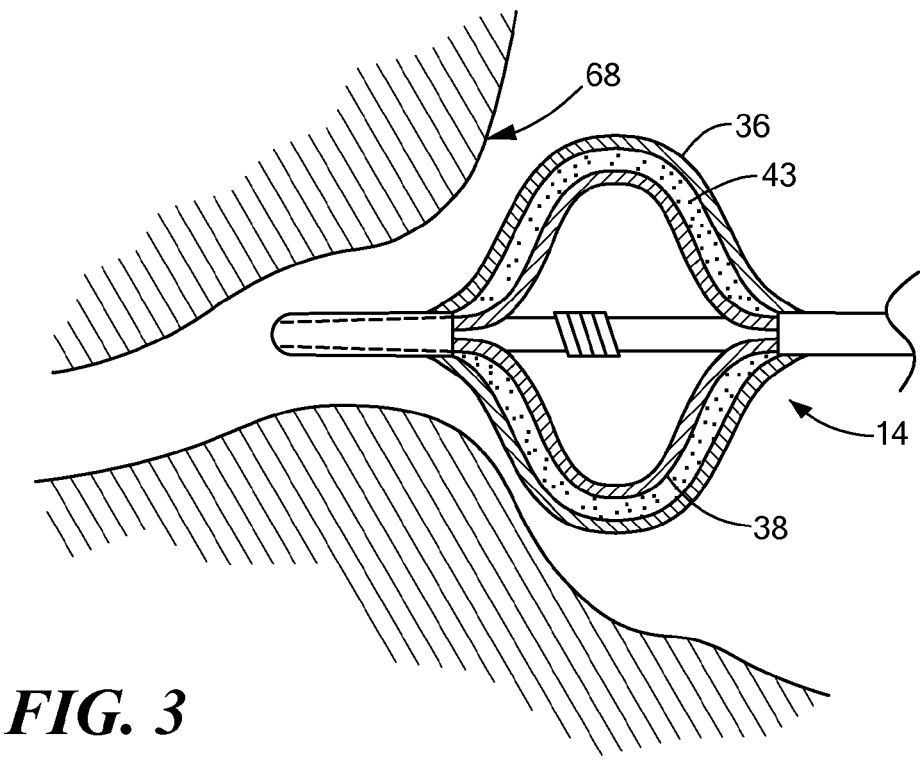
FIG. 3 is an illustration of an exemplary use of a medical device constructed in accordance with the principles of the present invention.
Figure 4:
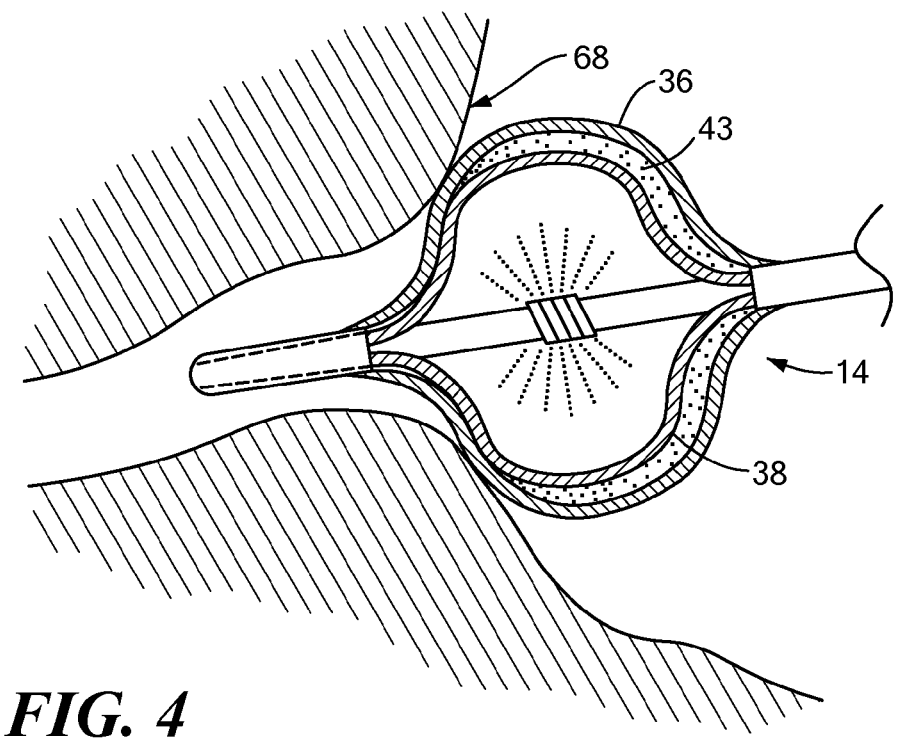
FIG. 4 is another illustration of an exemplary use of a medical device constructed in accordance with the principles of the present invention.

In an exemplary method of use, the medical system 10 may be used to deliver therapeutic treatment to a targeted tissue area. Now referring to FIGS. 3-4, in particular, the elongate body 26 of the medical device 14 may be introduced into and routed through the vascular system of a patient to a location where the treatment region 34 is proximate to a target tissue site 68, such as the heart. Traversing the vasculature and positioning of the treatment region 34 may be aided by imaging techniques (fluoroscopy, etc.) as known in the art. Once in the vicinity of the targeted tissue, a distal portion of the treatment region 34 may be advanced at least partially into contact with the targeted tissue. For example, the expandable elements of the medical device 14 may be positioned to contact and/or otherwise occlude a pulmonary vein opening in the atrium of the heart. Contacting the targeted tissue may result in the deformation of the outer, first expandable element 36 as well as the compression and/or movement of the interstitial agent 43 towards a proximal portion of the interstitial region 40. As additional force is applied and/or the treatment region 34 is advanced towards the pulmonary vein or other tissue opening, the first expandable element 36 may be substantially collapsed onto the inner, second expandable element 38. As discussed above, the second expandable element 38 may have an increased rigidity as that of the first expandable element 36, ensuring that the medical device 14 does not proceed undesirably into the pulmonary vein or targeted orifice.

Once firmly in position, treatment with the medical device 14 may be initiated. For example, a coolant or refrigerant, such as a cryogenic refrigerant, may be circulated into the second expandable element 38 for thermal exchange and/or ablation with the targeted tissue. The compressed or otherwise substantially adjacent contact between the first and second expandable elements towards the distal portion of the treatment region 34 can provide greater thermal conductivity for ablating tissue, while a more proximal portion of the second expandable element 38 may remain insulated from the surrounding environment by the interstitial agent 43 interposed between it and the first expandable element 36. In addition, the pliability of the first expandable element 36 and the presence of the interstitial agent 43 may provide an increased ability to seal or otherwise occlude a tissue opening where it transitions into the surrounding tissue area.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An intravascular catheter for treating an area of tissue, the catheter comprising:

a first expandable member disposed on a portion of the catheter;

a second expandable member disposed within the first expandable member to define an interstitial region therebetween, the second expandable member defining a cooling chamber;

a volume of an interstitial agent disposed within the interstitial region, the volume of the interstitial agent comprising a gel, saline, contrast solution or a mixture thereof having a viscosity between approximately 0.6 cP and approximately 2000 cP, the volume of the interstitial agent being configured such that at least partial contact between the first and second expandable members is achieved when at least a portion of the first expandable member is in contact with the area of tissue during a treatment procedure, the contact involving a compressive force against the tissue that is atraumatic to the tissue;

a coolant flow path in fluid communication with the cooling chamber;

a cryogenic coolant source in fluid communication with the coolant flow path, the cryogenic coolant being circulated within the cooling chamber when the first and second expandable members are at least partially in contact with each other during the treatment procedure; and an interstitial agent delivery flow path in fluid communication with the interstitial region, the at least partial contact between the first and second expandable members providing greater thermal conductivity of the first expandable member, such that the first expandable member reaches a temperature sufficient to cause tissue ablation when the cryogenic coolant is circulated through the cooling chamber.

2. The intravascular catheter of claim 1, wherein the interstitial agent has a thermal conductivity between approximately 0.1 W/(mK) and approximately 1 W/(mK).

3. The intravascular catheter of claim 1, wherein the interstitial agent is radiopaque.

4. The intravascular catheter of claim 1, further comprising a fluid ingress detection element in communication with the cooling chamber, the ingress detection element sensing an ingress of fluid into the cooling chamber from the interstitial region.

5. A medical device for thermally treating an area of tissue, the device comprising:
- an elongate body defining a distal portion and a proximal portion;
- a non-compliant expandable member disposed on the elongate body and defining a cooling chamber therein, the non-compliant expandable member having a first rigidity;
- a compliant expandable member disposed around the non-compliant expandable member to define an interstitial region therebetween, and wherein the compliant expandable member is sufficiently flexible so as to be at least partially in contact with the non-compliant expandable member when a compressive force is applied to the compliant expandable member during a tissue treatment procedure;
- a volume of a gel disposed within the interstitial region;
- a coolant flow path in fluid communication with the cooling chamber;
- a cryogenic coolant source in fluid communication with the coolant flow path; and
- an interstitial agent delivery flow path in fluid communication with the interstitial region, the interstitial agent delivery flow path being configured to deliver the volume of gel into the interstitial space, the volume of gel being configured such that the at least partial contact between the non-compliant and compliant expandable members is achieved when at least a portion of the compliant expandable member is in contact with the area of tissue during a treatment procedure, the compressive force between the tissue and the compliant expandable member being atraumatic to the tissue, the cryogenic coolant being circulated within the cooling chamber during the treatment procedure when the compliant expandable member and the non-compliant expandable member are at least partially in contact with each other,
- the at least partial contact between the non-compliant and compliant expandable members providing greater thermal conductivity of the compliant expandable member, such that the compliant expandable member is capable of reaching a temperature sufficient to cause tissue ablation.

6. The medical device of claim 5, wherein the compliant expandable member is attached to at least one of the elongate body and the non-compliant expandable member, thereby sealing the interstitial region.

7. The medical device of claim 5, wherein the gel has a viscosity between approximately 0.6 cP and approximately 2000 cP.

8. The medical device of claim 7, wherein the gel has a thermal conductivity between approximately 0.1 W/(mK) and approximately 1 W/(mK).

9. The intravascular medical device of claim 5, further comprising a fluid ingress detection element in communication with the cooling chamber, the ingress detection element sensing an ingress of fluid into the cooling chamber from the interstitial region.

* * * * *